(12) United States Patent
Karunasiri

(10) Patent No.: US 9,717,908 B2
(45) Date of Patent: Aug. 1, 2017

(54) SYSTEMS AND METHODS FOR DETECTING A COMPLIANCE STATE OF A CURRENT SOURCE INCLUDED IN A COCHLEAR IMPLANT

(71) Applicant: ADVANCED BIONICS AG, Staefa (CH)

(72) Inventor: R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,027

(22) PCT Filed: Feb. 24, 2014

(86) PCT No.: PCT/US2014/018099
§ 371 (c)(1),
(2) Date: Mar. 22, 2016

(87) PCT Pub. No.: WO2015/126432
PCT Pub. Date: Aug. 27, 2015

(65) Prior Publication Data
US 2016/0228703 A1 Aug. 11, 2016

(51) Int. Cl.
*A61N 1/36* (2006.01)
(52) U.S. Cl.
CPC .................. *A61N 1/36032* (2013.01)
(58) Field of Classification Search
None
See application file for complete search history.

(56) References Cited

U.S. PATENT DOCUMENTS 7,444,181 B2 10/2008 Shi et al.
8,527,062 B2 9/2013 Dai et al.
(Continued)

FOREIGN PATENT DOCUMENTS

EP 1121177 12/2005
WO WO-2007/070727 6/2007
(Continued)

OTHER PUBLICATIONS

International Search Report and Written Opinion received in International Application No. PCT/US14/018099, dated Oct. 17, 2014.

*Primary Examiner* — Brian T Gedeon
(74) *Attorney, Agent, or Firm* — ALG Intellectual Property, LLC

(57) ABSTRACT

An exemplary cochlear implant may include 1) a current source tied to a voltage supply and having an output that is electrically coupled to an electrode included in a plurality of electrodes, 2) a mirrored current source associated with the current source and that is commanded to output a commanded current, 3) a reference load coupled to an output of the mirrored current source and that forces the mirrored current source into an out-of-compliance state in which the mirrored current source outputs a reference current that is a predetermined percentage lower than the commanded current, the reference current resulting in a dynamic reference voltage at the output of the mirrored current source, and 4) a comparator that compares a voltage at the output of the current source with the dynamic reference voltage, and outputs a signal based on the comparison. Corresponding systems and methods are also described.

20 Claims, 10 Drawing Sheets

(56) References Cited

U.S. PATENT DOCUMENTS

| | | |
|---|---|---|
| 8,781,598 B2 | 7/2014 | Shi et al. |
| 2007/0135868 A1 | 6/2007 | Shi et al. |
| 2011/0160799 A1 | 6/2011 | Mishra et al. |
| 2011/0190849 A1 | 8/2011 | Faltys et al. |
| 2013/0073008 A1 | 3/2013 | Ternes et al. |
| 2014/0018883 A1 | 1/2014 | Shi et al. |

FOREIGN PATENT DOCUMENTS

| | | |
|---|---|---|
| WO | WO-2008/060343 | 5/2008 |
| WO | WO-2013/013269 | 1/2013 |

US 9,717,908 B2

SYSTEMS AND METHODS FOR DETECTING A COMPLIANCE STATE OF A CURRENT SOURCE INCLUDED IN A COCHLEAR IMPLANT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

In a typical cochlear implant system, positive and negative current sources are connected to a stimulating electrode. These current sources are driven by limited supply voltages and, as a result, are susceptible to a condition in which the current source may be in an out-of-compliance state. Such an out-of-compliance state may occur as a result of, for example, a relatively high electrode impedance and/or a relatively high value of commanded output current pulses. When in the out-of-compliance state, the current sources are unable to output a commanded amount of current due to a lack of voltage headroom. This may result in signal distortion and/or audio quality degradation, which can be annoying and/or disconcerting to the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for detecting a compliance state of a current source included in a cochlear implant system are described herein. As will be described in more detail below, a cochlear implant electrically coupled to a plurality of electrodes may be implanted within a patient and may include 1) a current source tied to a voltage supply and having an output that is electrically coupled to an electrode included in the plurality of electrodes, 2) a mirrored current source associated with the current source and that is commanded to output a commanded current, 3) a reference load coupled to an output of the mirrored current source and that forces the mirrored current source into an out-of-compliance state in which the mirrored current source outputs a reference current that is a predetermined percentage lower than the commanded current, the reference current resulting in a dynamic reference voltage at the output of the mirrored current source, and 4) a comparator that compares a voltage at the output of the current source with the dynamic reference voltage and outputs a signal based on the comparison.

The systems and methods described herein may advantageously allow for detection of a compliance state associated with a current source during operation and/or calibration of the cochlear implant system. By detecting, for example, that the current source is in an out-of-compliance state, the systems and methods described herein may facilitate dynamic adjustment (e.g., an increase) of an amount of voltage provided by a voltage supply associated with the current source in order to bring the current source back into compliance (i.e., provide enough voltage headroom for the current source to be able to output a commanded current). In so doing, it may be possible to minimize or avoid signal distortion and/or audio quality degradation that may otherwise occur due to the out-of-compliance state of the current source. Furthermore, by detecting that the current source is operating below the compliance limit associated with the current source, the systems and methods described herein may dynamically reduce the amount of voltage provided by the voltage supply, thereby conserving power and resulting in improved battery life for the cochlear implant system. Other benefits of the systems and methods described herein will be made apparent herein.

Figure 1:
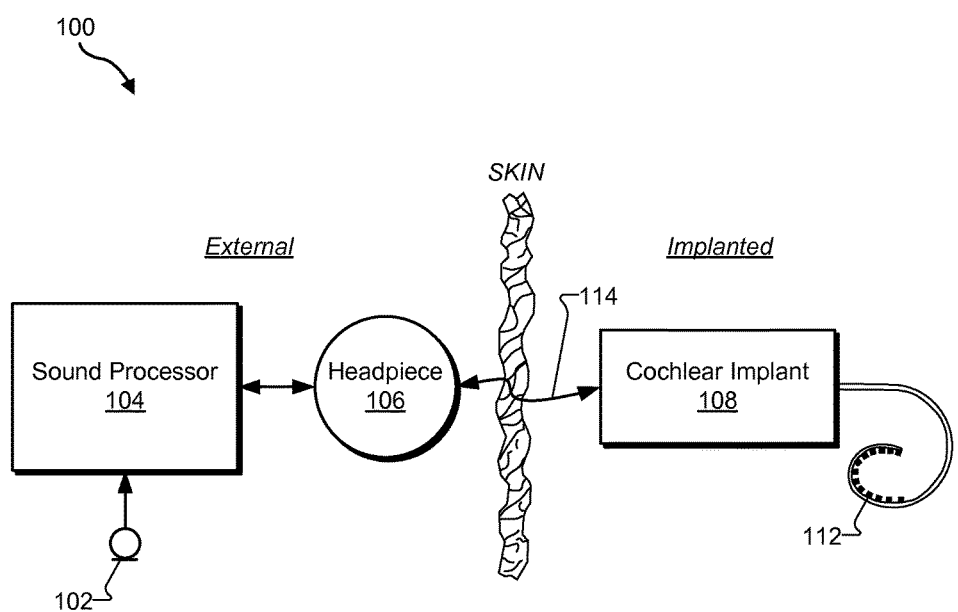
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or RF power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or RF power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112. For ease of explanation, the following description refers to one of the electrodes included in electrodes 112.

Figure 2:
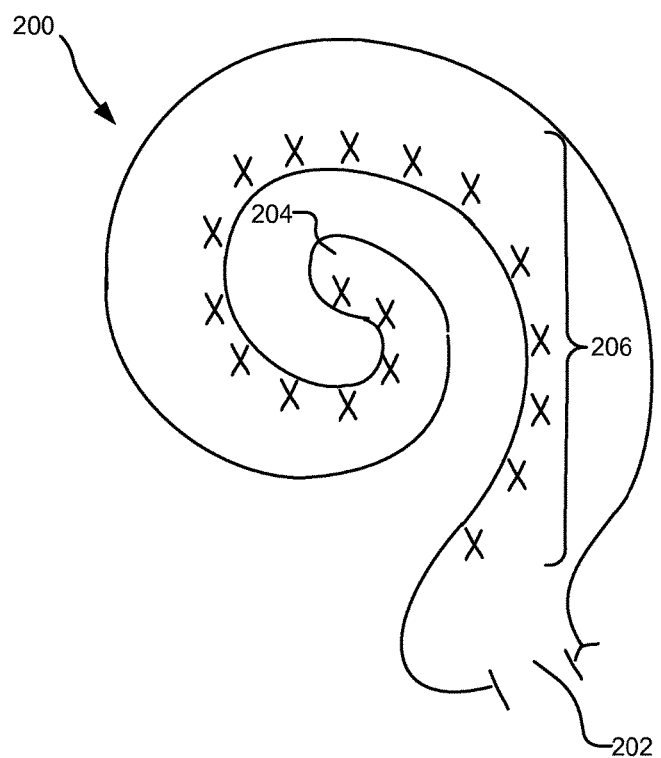
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
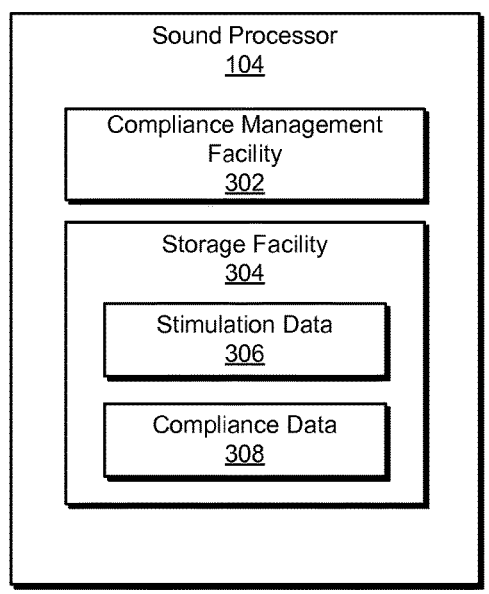
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a compliance management facility 302 ("management facility 302") and a storage facility 304, which may be in communication with one another using any suitable communication technologies. Storage facility 304 may be configured to maintain stimulation data 306 generated and/or used by compliance management facility 302, and compliance data 308 measured and/or used by compliance management facility 302. Storage facility 304 may maintain additional or alternative data as may serve a particular implementation. One or more of facilities 302 and 304 may include a computing device or processor configured to perform one or more of the functions described herein. Management facility 302 will now be described in more detail.

A current source provided in a cochlear implant is typically driven by a limited supply voltage from a voltage supply coupled to the current source. As used herein, the expression "limited supply voltage" refers to how there may be only a predefined amount of voltage allocated to the voltage supply at any given time. The allocated voltage typically includes an amount of voltage that may be used to drive the current generated by the current source and an amount of voltage necessary to operate the current source (which amount may be referred to as headroom voltage). In certain circumstances, the current source may be commanded to output an amount of current that requires more voltage than is available from the voltage supply (e.g., the commanded current requires an amount of voltage that includes all of the voltage available to drive the current as well as some or all of the voltage necessary to operate the current source). As such, the current source enters an "out-of-compliance state" in which the current source is unable to output the commanded amount of current. When this occurs, a cochlear implant patient may experience signal distortion and/or audio quality degradation as the current source tries to but cannot output the commanded current. Accordingly, it may be desirable to determine when a current source enters the out-of-compliance state to facilitate making suitable adjustments to the cochlear implant system (e.g., by increasing the voltage allocated to the voltage supply in order to bring the current source back into compliance).

To this end, management facility 302 may be configured to detect a compliance state associated with a current source included in cochlear implant 108. For example, management facility 302 may detect each time a current source included in the cochlear implant 108 enters an out-of-compliance state. As used herein, an "out-of-compliance state" refers to a condition in which a current source is unable to generate a commanded amount of current due to insufficient voltage headroom. Conversely, the current source may be "within compliance" or operate in an "in-compliance state" when the current source is able to generate a commanded amount of current.

To detect a compliance state associated with a current source, management facility 302 may utilize reference circuitry included in cochlear implant 108 that is configured to output a dynamic reference voltage. Examples of how the dynamic reference voltage may be generated by the reference circuitry and utilized by management facility 302 are provided herein.

Figure 4:
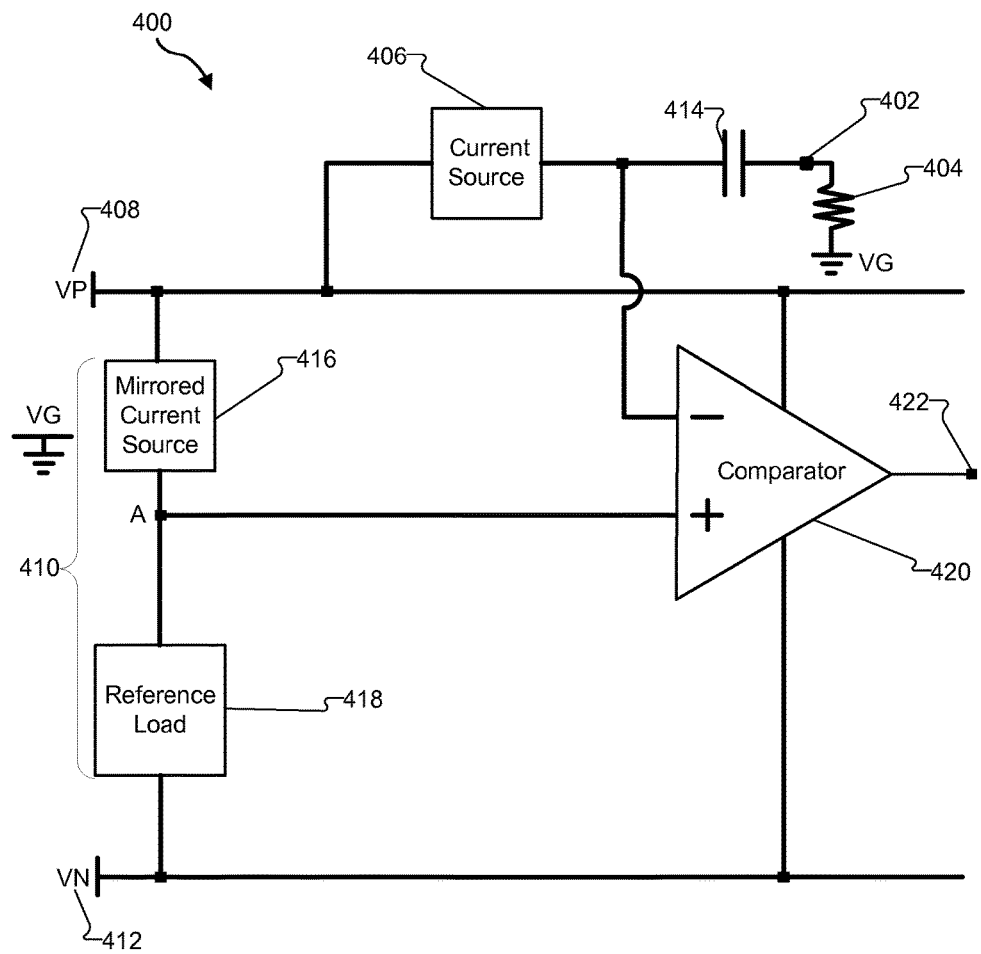
FIGS. 4-6 illustrate exemplary current generation circuits according to principles described herein.

In certain implementations, management facility 302 may be configured to detect a compliance state associated with a positive current source provided in a cochlear implant (e.g., cochlear implant 108). To illustrate, FIG. 4 shows an exemplary current generation circuit 400 associated with a particular electrode 402 (which may be one of electrodes 112, for example) and that may be included within cochlear implant 108. A similar current generation circuit 400 may be included within cochlear implant 108 for each electrode included in electrodes 112.

Electrode 402 may have an electrode impedance associated therewith. This electrode impedance is represented in FIG. 4 by resistor 404 and, in some cases, may vary over time depending on a variety of factors. Such variance in electrode impedance may affect whether or not a current source associated with electrode 402 enters an out-of-compliance state when commanded to output a particular current.

As shown in FIG. 4, current generation circuit 400 may include a positive current source 406 (e.g., a PDAC current source) tied to a positive voltage supply 408 (labeled "VP" in FIG. 4) and reference circuitry 410 tied to a negative voltage supply 412 (labeled "VN" in FIG. 4). As shown, the positive voltage supply 408 and the negative voltage supply 412 are provided with respect to a ground voltage labeled VG in FIG. 4. It will be recognized that the current generation circuit components shown in FIG. 4 are merely representative of the many different components that may be included in current generation circuit 400 and that current generation circuit 400 may include additional or alternative components as may serve a particular implementation. In addition to being used by management facility 302 to determine a compliance state of current source 406, current generation circuit 400 may also be configured to generate an electrical stimulation pulse that may represent an audio signal and that may be applied to a patient (e.g., to a location within the cochlea of the patient) by way of electrode 402 and a DC blocking capacitor 414.

In the example illustrated in FIG. 4, reference circuitry 410 may include a mirrored current source 416 that is associated with current source 406 and that is commanded to output a commanded current. As used herein, a "mirrored current source" refers to a current source that exhibits the same characteristics as another current source. In the example illustrated in FIG. 4, mirrored current source 416 exhibits the same characteristics as current source 406 (e.g., conditions that cause mirrored current source 416 to enter an out-of-compliance state also cause current source 406 to enter an out-of-compliance state).

Mirrored current source 416 may have any suitable configuration. In some examples, current source 406 may comprise a plurality of unit cells (e.g., one thousand unit cells) that each may be configured to output a predefined amount of current. In such a configuration, mirrored current source 416 may comprise only a single unit cell corresponding to the plurality of unit cells that make up current source 406. By forming part of the unit cells of current source 406, mirrored current source 416 may exhibit the same characteristics as current source 406. Alternatively, mirrored current source 416 may be provided in addition to the plurality of unit cells, but may be operationally equivalent to the unit cells of current source 406 such that mirrored current source 416 and current source 406 exhibit the same characteristics.

As illustrated in FIG. 4, reference circuitry 410 may also include a reference load 418 coupled to an output of mirrored current source 416. Reference load 418 may have any suitable configuration. For example, reference load 418 may be configured to force mirrored current source 416 into an out-of-compliance state in which mirrored current source 416 outputs a reference current that is a predetermined percentage lower than a commanded current. To illustrate, management facility 302 may command that mirrored current source 416 output a current of 1 µA. However, reference load 418 may be configured so as to force mirrored current source 416 to output only 0.90 µA (i.e., an amount that is ten percent lower than the commanded current). The reference current may result in a dynamic reference voltage being provided at the output of mirrored current source 416 (i.e., at the node labeled "A" between mirrored current source 416 and reference load 418). The dynamic reference voltage corresponds to a voltage that occurs at the output of mirrored current source 416 when mirrored current source 416 is out-of-compliance and can only output a current that is the predetermined percentage lower than the commanded current. The dynamic reference voltage may be considered "dynamic" because the value of the dynamic reference voltage is representative of the present conditions associated with cochlear implant 108 and may change as the conditions associated with cochlear implant 108 change (e.g., as temperature, power supply voltages, and/or reference bias current changes). Specific examples of reference loads and how they may be implemented are provided herein.

Because the mirrored current source 416 exhibits the same characteristics as the current source 406, the dynamic reference voltage may be compared to a voltage at the output of current source 406 to determine when current source 406 is out-of-compliance. To this end, a comparator 420 may be provided within cochlear implant 108 that compares a voltage at the output of the current source 406 with the dynamic reference voltage output by the mirrored current source 416. The comparator 420 may be provided in any suitable manner. In some examples, a single comparator may be provided for all of electrodes 112. The single comparator may be selectively coupled to a particular electrode of electrodes 112 in any suitable manner. In other examples, a comparator may be provided for each electrode included in electrodes 112.

In the example illustrated in FIG. 4, the dynamic reference voltage is detected at the "+" input of comparator 420 and the voltage at the output of current source 406 is detected at the "−" input of comparator 420. Based on the detected voltages, comparator may output a signal that is indicative of the compliance state of current source 406. The signal may be output by comparator 420 in any suitable manner. In certain examples, the signal may be output by comparator 420 in one of a first state and a second state at output 422 depending on whether the voltage at the output of current source 406 is greater than the dynamic reference voltage. The first state may be indicative of when current source 406 is in-compliance, and the second state may be indicative of when current source 406 is out-of-compliance. For example, comparator 420 may output the signal in the first state when the voltage at the output of current source 406 is lower than the dynamic reference voltage. This means that current source 406 is operating in an in-compliance state in which current source 406 can output a commanded current level. Alternatively, comparator 420 may output the signal in the second state when the voltage at the output of current source 406 is greater than the dynamic reference voltage. This means that current source 406 is operating in an out-of-compliance state in which current source 406 cannot output a commanded current level.

Returning to FIG. 3, management facility 302 may direct cochlear implant 108 to enable mirrored current source 416 such that mirrored current source 416 operates in an out-of-compliance state. Management facility 302 may enable the mirrored current source 416 in any suitable manner. For example, management facility 302 may enable mirrored current source 416 so as to continually generate a dynamic reference voltage associated with the out-of-compliance state during operation of cochlear implant 108. Alternatively, management facility 302 may enable mirrored current source 416 for a predetermined amount of time to generate the dynamic reference voltage.

While the dynamic reference voltage is provided to comparator 420, management facility 302 may direct cochlear implant 108 to enable current source 406 in order to generate a current (i.e., a commanded current) that is provided to electrode 402 and that results in a voltage at the output of current source 406. Current source 406 may be enabled in any suitable manner. In certain examples, current source 406 may be enabled as part of a calibration procedure during which management facility 302 determines how much voltage to allocate to a voltage supply (e.g., positive voltage supply 408). Additionally or alternatively, current source 406 may be enabled during a normal operation of cochlear implant system 100 (e.g., during a patient's normal daily activities).

The current provided by current source 406 may result in an electrical stimulation pulse that may represent an audio signal and that may be applied to a patient (i.e., to a location within the cochlea by way of an electrode coupled to cochlear implant 108). During normal operation of cochlear implant system 100 and/or during a calibration procedure, a plurality of electrical stimulation pulses may be applied to the patient. Management facility 302 may detect a signal output from comparator 420 after each stimulation pulse to detect when the signal output from comparator 420 flips from the first state to the second state. As mentioned, the flipping of the signal from the first state to the second stated may occur as a result of the voltage at the output of current source 406 being greater than the dynamic reference voltage. Management facility 302 may determine that current source 406 is out-of-compliance when the signal output from comparator 420 flips from the first state to the second state.

An out-of-compliance state detected in current source 406 may indicate that positive voltage supply 408 has not been allocated enough voltage to meet the present needs of current source 406. Accordingly, in certain examples, management facility 302 may direct cochlear implant 108 to adjust an amount of voltage allocated to positive voltage supply 408 based on whether the signal output by comparator 420 is in the first state or the second state. For example, if the signal output by comparator 420 is in the second state (i.e., current source 406 is out-of-compliance), management facility 302 may direct cochlear implant 108 to increase the amount of voltage allocated to positive voltage supply 408. In so doing, it may be possible for management facility 302 to dynamically determine an optimal voltage to allocate to positive voltage supply 408 as the conditions associated with cochlear implant 108 change. In certain examples, management facility 302 may adjust the amount of voltage allocated to positive voltage supply 408 after a single detection of current source 406 being out-of-compliance. Alternatively, management facility 302 may wait until the signal output from comparator 420 flips from the first state to the second state a predetermined number of times before increasing the amount of voltage allocated to positive voltage supply 408.

During normal operation of cochlear implant system 100 and/or during a calibration procedure, management facility 302 may detect that current source 406 does not enter an out-of-compliance state for a predetermined period of time (e.g., none of the voltages detected at the output of current source 406 during the predetermined time period were greater than the dynamic reference voltage). Such a circumstance may indicate that more voltage has been allocated to positive voltage supply 408 than is presently needed to adequately drive current from current source 406. Accordingly, in certain implementations, management facility 302 may decrease the amount of voltage allocated to positive voltage supply 408 based the signal output by comparator 420. For example, management facility 302 may detect that the signal output by comparator 420 has remained in the first state for a predetermined amount of time. After the predetermined amount of time elapses, management facility 302 may direct cochlear implant 108 to decrease the amount of voltage allocated to positive voltage supply 408. In so doing, management facility 302 may reduce power consumption by the cochlear implant 108 and, as a result, maximize the life of a battery associated with cochlear implant system 100. It is understood that management facility 302 may dynamically increase or decrease the amount of voltage allocated to positive voltage supply 408 as many times and as often as suitable to respond to changes that may occur in the conditions associated with cochlear implant system 100.

Figure 5:
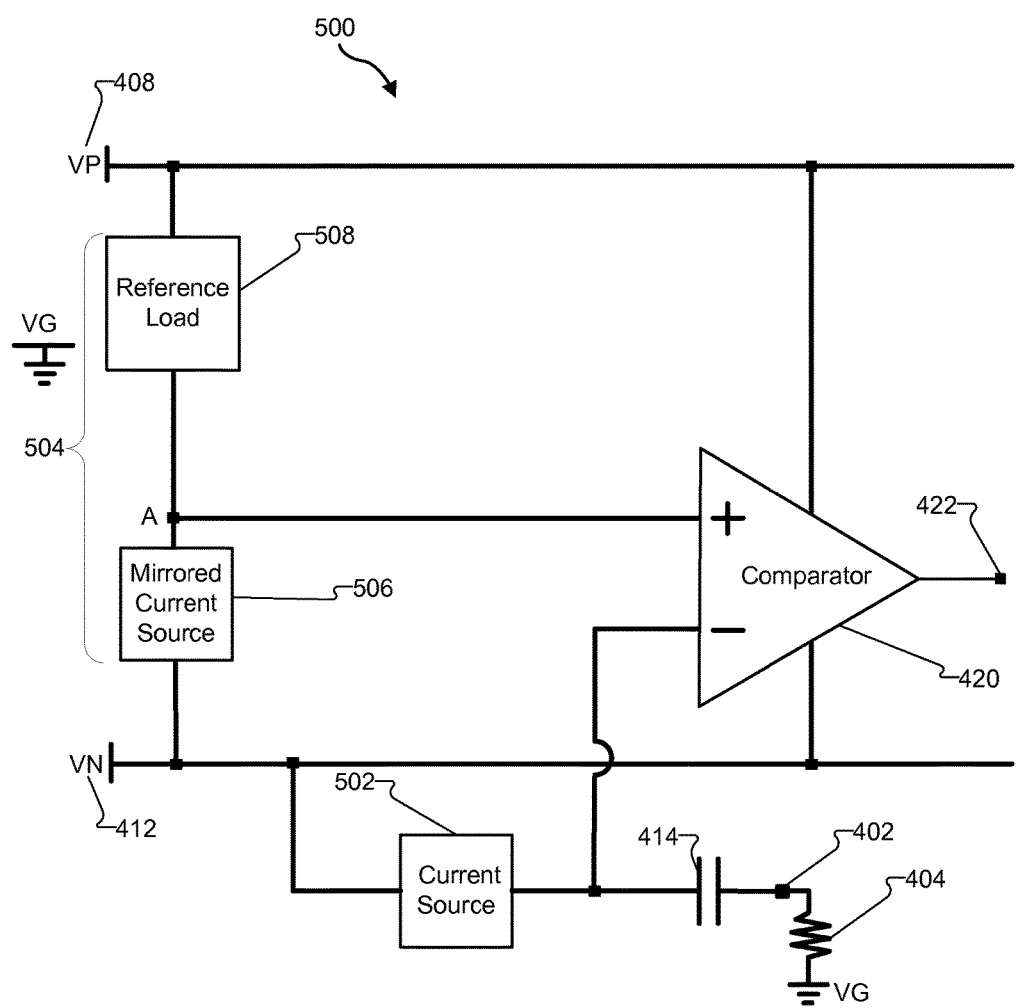

In certain implementations, management facility 302 may be configured to detect a compliance state associated with a negative current source provided in a cochlear implant (e.g., cochlear implant 108). To illustrate, FIG. 5 shows another exemplary current generation circuit 500 that may be included in cochlear implant 108. Current generation circuit 500 is similar to current generation circuit 400 except that, in current generation circuit 500, a negative current source 502 (e.g., an NDAC current source) is coupled to negative voltage supply 412 and reference circuitry 504 is coupled to positive voltage supply 408. It will be recognized that although FIG. 5 shows that the same comparator 420 is included in both current generation circuit 400 and current generation circuit 500, current generation circuit 500 may include a different comparator as may sever a particular implementation.

As illustrated in FIG. 5, reference circuitry 504 may include a mirrored current source 506 and a reference load 508 coupled to an output of mirrored current source 506. It will be recognized that the current generation circuit components shown in FIG. 5 are merely representative of the many different components that may be included in current generation circuit 500 and that current generation circuit 500 may include additional or alternative components as may serve a particular implementation. The exemplary current generation circuit components illustrated in FIG. 5 may operate in a manner similar to those described above with respect to FIG. 4.

For example, comparator 420 may output a signal in one of a first state and a second state at output 422 depending on whether the voltage at the output of current source 502 is less than the dynamic reference voltage. The first state may be indicative of when current source 502 is in-compliance, and the second state may be indicative of when current source 502 is out-of-compliance. For example, comparator 420 may output the signal in the first state when the voltage at the output of current source 502 is greater than the dynamic reference voltage. This means that current source 502 is operating in an in-compliance state in which current source 502 can output a commanded current level. Alternatively, comparator 420 may output the signal in the second state when the voltage at the output of current source 502 is less than the dynamic reference voltage. This means that current source 502 is operating in an out-of-compliance state in which current source 502 cannot output a commanded current level.

Figure 6:
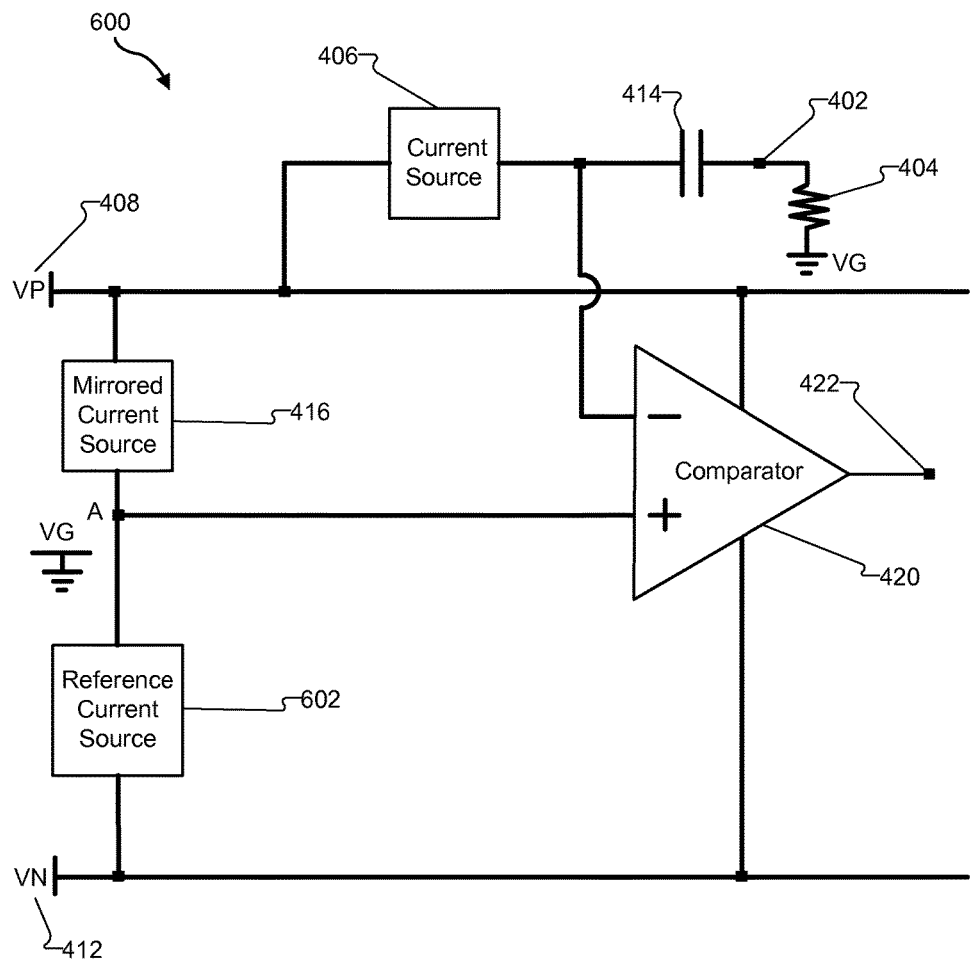

Reference loads, such as reference loads 418 and 508 described in FIGS. 4 and 5, may have any suitable configuration. In certain implementations, a reference load may comprise a reference current source that is opposite in polarity to a mirrored current source. For example, FIG. 6 shows an exemplary current generation circuit 600 that is similar to current generation circuit 400 except that, in current generation circuit 600, a reference current source 602 is provided as the reference load. In the example illustrated in FIG. 6, reference current source 602 may have a negative polarity (e.g., reference current source 602 may be an NDAC current source) and mirrored current source 416 may have a positive polarity (e.g., mirrored current source 416 may be a PDAC current source). Reference current source 602 may be configured to output a first current that is the predetermined percentage lower than a current that mirrored current source 416 is commanded to output. This configuration results in a condition in which mirrored current source 416 enters an out-of-compliance state.

To illustrate, mirrored current source 416 may be commanded to output 1 µA of current and reference current source 602 may be configured to output 0.85 µA of current. Because reference current source 602 is in series with mirrored current source 416, mirrored current source 416 will try to output 1 µA of current, but will only be able to output 0.85 µA of current (i.e., a current that is fifteen percent lower than the commanded current). As such, reference current source 602 may force mirrored current source 416 into the out-of-compliance state. The preceding example is provided for illustrative purposes only. It is understood that reference current source 602 may be configured to output any suitable amount of current less than the commanded current in other implementations.

Similarly, reference load 508 shown in FIG. 5 may be implemented by a current source opposite in polarity to mirrored current source 506. For example, as mentioned above, mirrored current source 506 may be implemented by an NDAC current source (e.g., an NDAC unit cell). In this example, reference load 508 may be implemented by a PDAC current source.

In certain implementations, it may be desirable to selectively adjust the predetermined percentage that the reference current is lower than the commanded current. To this end, in some examples, the reference load (e.g., reference load 418 and/or reference load 508) may comprise a plurality of selectable reference current sources arranged in parallel one with another. In this configuration, it may be possible to selectively adjust the amount of current output by the reference load.

Figure 7:
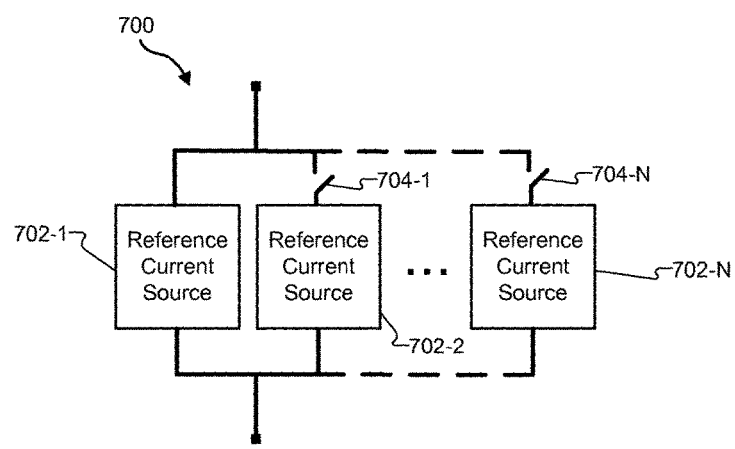
FIG. 7 illustrates an exemplary reference load according to principles described herein.

FIG. 7 illustrates an exemplary reference current source configuration 700 of a reference load that may be provided instead of the single reference current source 602 illustrated in FIG. 6. As illustrated in FIG. 7, a plurality of reference current sources 702 (e.g., reference current sources 702-1 through 702-N) may be provided in parallel with respect to each other. Each reference current source 702 may be configured to output a respective current. To illustrate, reference current source 702-1 may be configured to output 0.85 µA of current whereas reference current source 702-2 may be configured to output 0.05 µA of current. By selectively enabling one or more of reference current sources 702, a desired total amount of current may be output by reference current sources 702. For example, by enabling both reference current source 702-1 and reference current source 702-2, the total current output by reference current source configuration 700 is 0.90 µA. The preceding example is provided for illustrative purposes only. It is understood that reference current sources 702 may be configured to output other amounts of current as may suit other implementations.

Management facility 302 may selectively enable one or more of reference current sources 702 in any suitable manner. For example, as shown in reference current source 702-2 may be associated with a switch 704-1 that, when closed, is configured to selectively enable reference current source 702-2. Likewise, switch 704-N may be closed to selectively enable reference current source 702-N. Switches 704-2 through 704-N may be implemented in any suitable manner as may suit a particular implementation. For example, switch 704-1 may be implemented by a physical switch and/or any suitable software component. Reference current source 702-2 may be configured such that closing switch 704-1 results in decreasing the predetermined percentage by a pre-defined amount. That is, in the example discussed above, when switch 704-1 is open, the current provided by reference current source configuration 700 is 0.85 μA. However, when switch 704-1 is closed, the current provided by reference current source configuration 700 is 0.90 μA (i.e., the predetermined percentage decreased from fifteen percent to ten percent). The preceding example is provided for illustrative purposes only. It is understood that reference current source configuration 700 may be configured to output any suitable amount of current less than the commanded current in other implementations.

In certain alternative implementations, the reference load (e.g., reference loads 418 and/or 508) may include at least one resistor that has a resistance value that is sufficient to force the mirrored current source into the out-of-compliance state.

Figure 8:
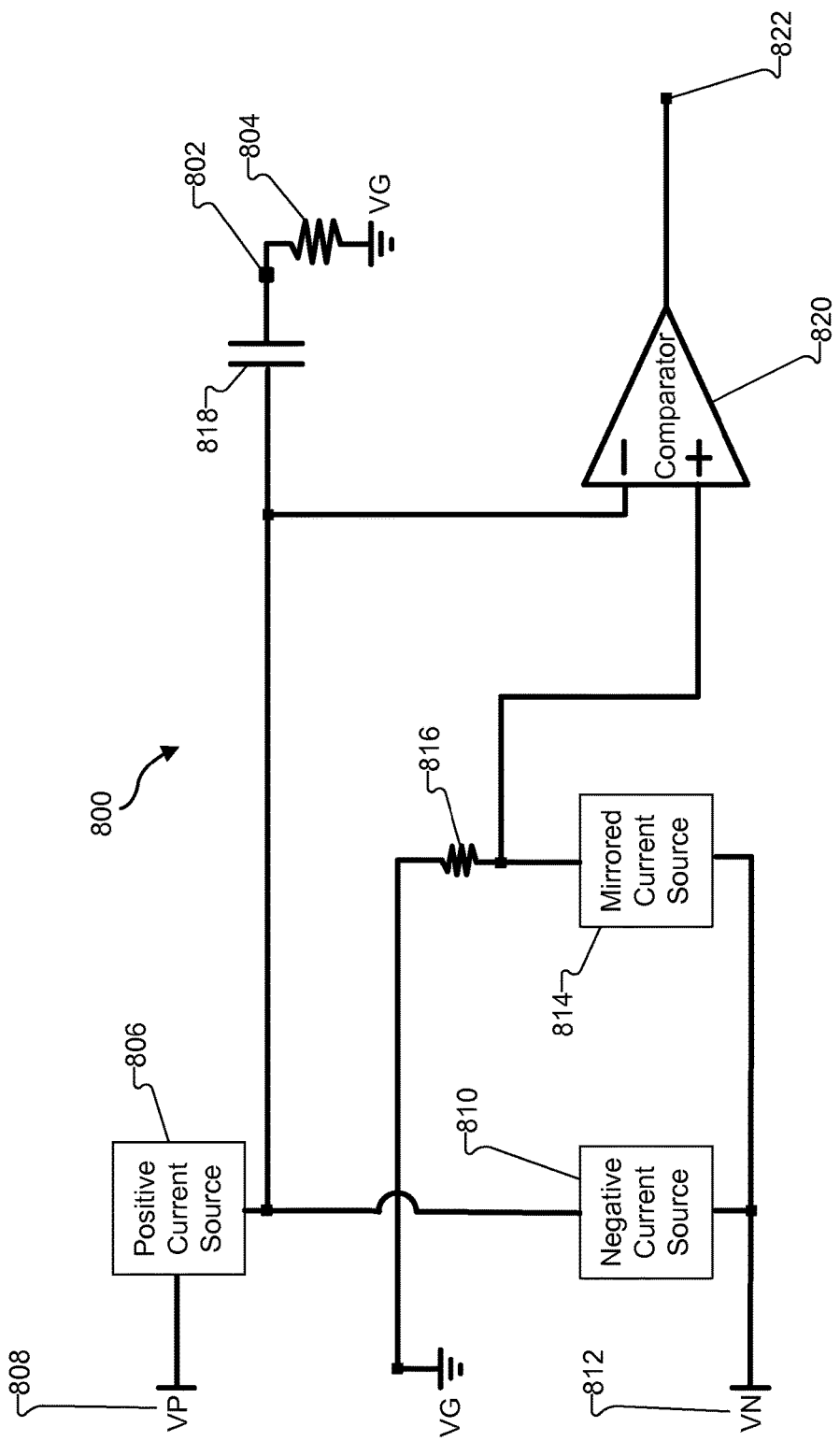
FIGS. 8-9 illustrates additional exemplary current generation circuits according to principles described herein.

To illustrate, FIG. 8 shows an exemplary current generation circuit 800 associated with a particular electrode 802 (which may be one of electrodes 112, for example) and that may be included within cochlear implant 108. As described above, electrode 802 may have an electrode impedance associated therewith, which is represented in FIG. 8 by resistor 804.

Current generation circuit 800 may include a positive current source 806 tied to a positive voltage supply 808 (labeled "VP" in FIG. 8) and a negative current source 810 tied to a negative voltage supply 812 (labeled "VN" in FIG. 8). It will be recognized that the current generation circuit components shown in FIG. 8 are merely representative of the many different components that may be included in current generation circuit 800 and that current generation circuit 800 may include additional or alternative components as may serve a particular implementation.

Current generation circuit 800 may also include a mirrored current source 814 that is a mirror of negative current source 810 and that is provided in series with a resistor 816. Resistor 816 may be provided as the reference load instead of, for example, a reference current source. The resistance value of resistor 816 may be selected so as to be large enough to force negative current source 810 to enter an out-of-compliance state. To illustrate, if mirrored current source 814 is commanded to output a current of 1 μA, the resistance value of resistor may be selected so as to force mirrored current source 814 to only be able to output, for example, 0.80 μA. In certain implementations, additional resistors may be provided in series between resistor 816 and mirrored current source 814 to facilitate adjustment of the predetermined percentage that the reference current is lower than the commanded current. When additional resistors are provided, switches may be provided in any suitable manner to allow management facility 302 to selectively enable/disable the additional resistors.

Current generation circuit 800 may also be configured to generate an electrical stimulation pulse that may represent an audio signal and that may be applied to a patient (e.g., to a location within the cochlea of the patient) by way of electrode 802 and a DC blocking capacitor 818.

As illustrated in FIG. 8, an output of each of positive current source 806 and mirrored current source 814 may be coupled to a comparator 820 that is configured to output a signal at output 822. Management facility 302 may utilize the signal detected at output 822 of comparator 820 in any suitable manner, such as described herein.

Figure 9:
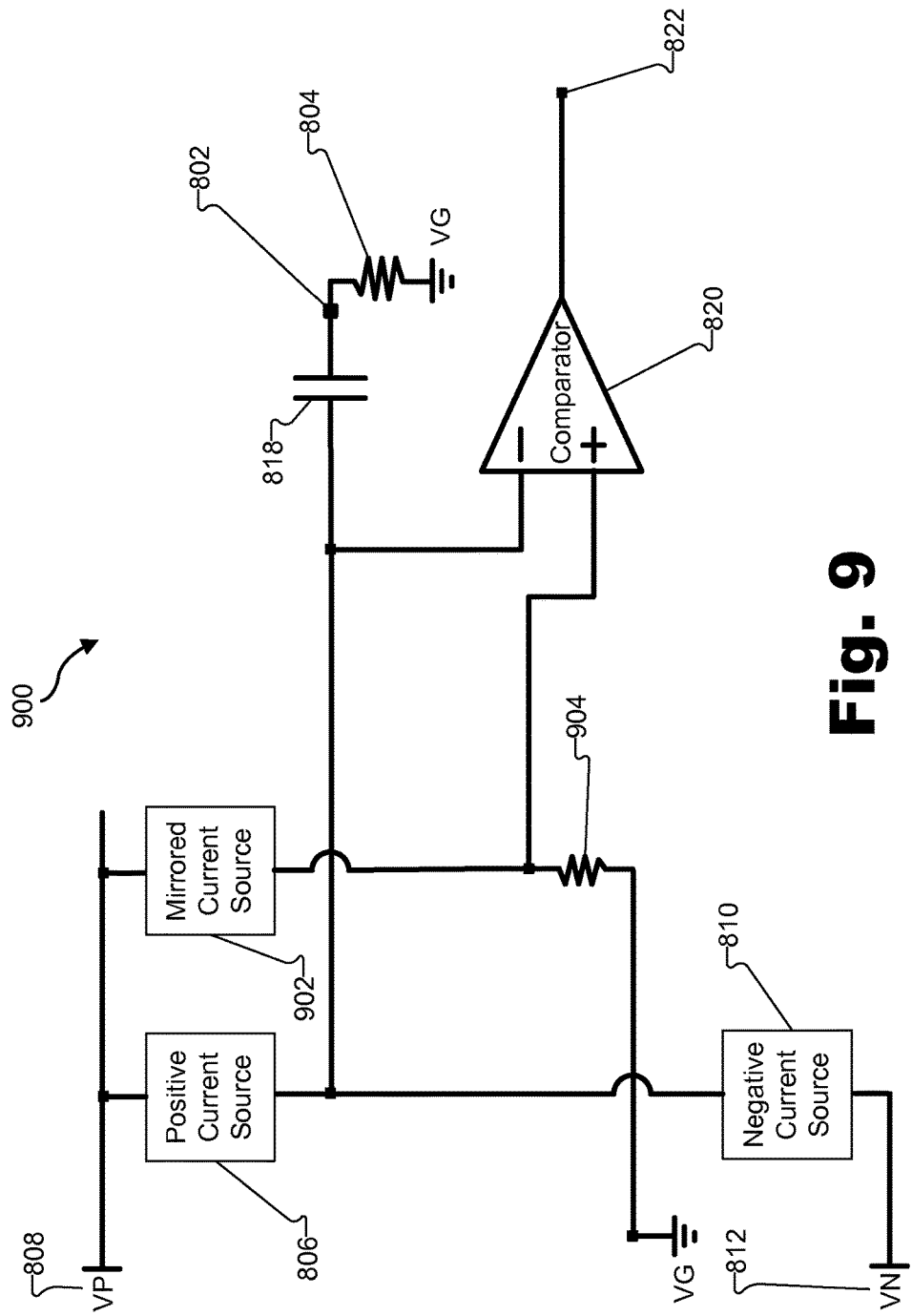

FIG. 9 shows another exemplary current generation circuit 900 that may be included in cochlear implant 108. Current generation circuit 900 is similar to current generation circuit 800 except that, in current generation circuit 900, a mirrored current source 902 is a mirror of positive current source 806 instead of negative current source 810. As shown in FIG. 9, mirrored current source 902 is provided in series with a resistor 904 that may be selected so as to force mirrored current source 902 into an out-of-compliance state. It will be recognized that the current generation circuit components shown in FIG. 9 are merely representative of the many different components that may be included in current generation circuit 900 and that current generation circuit 900 may include additional or alternative components as may serve a particular implementation. The exemplary current generation circuit components illustrated in FIG. 9 may operate in a manner similar to those described above with respect to FIG. 8.

In certain implementations, the comparators described herein may be implemented by low power comparators. In these implementations, a voltage above a certain amount may damage an input of the comparator. To prevent damage to comparator, a voltage clamp (not shown) may be coupled, for example, at a node between negative current source 810 and mirrored current source 814 and may extend to an input of comparator 820.

Figure 10:
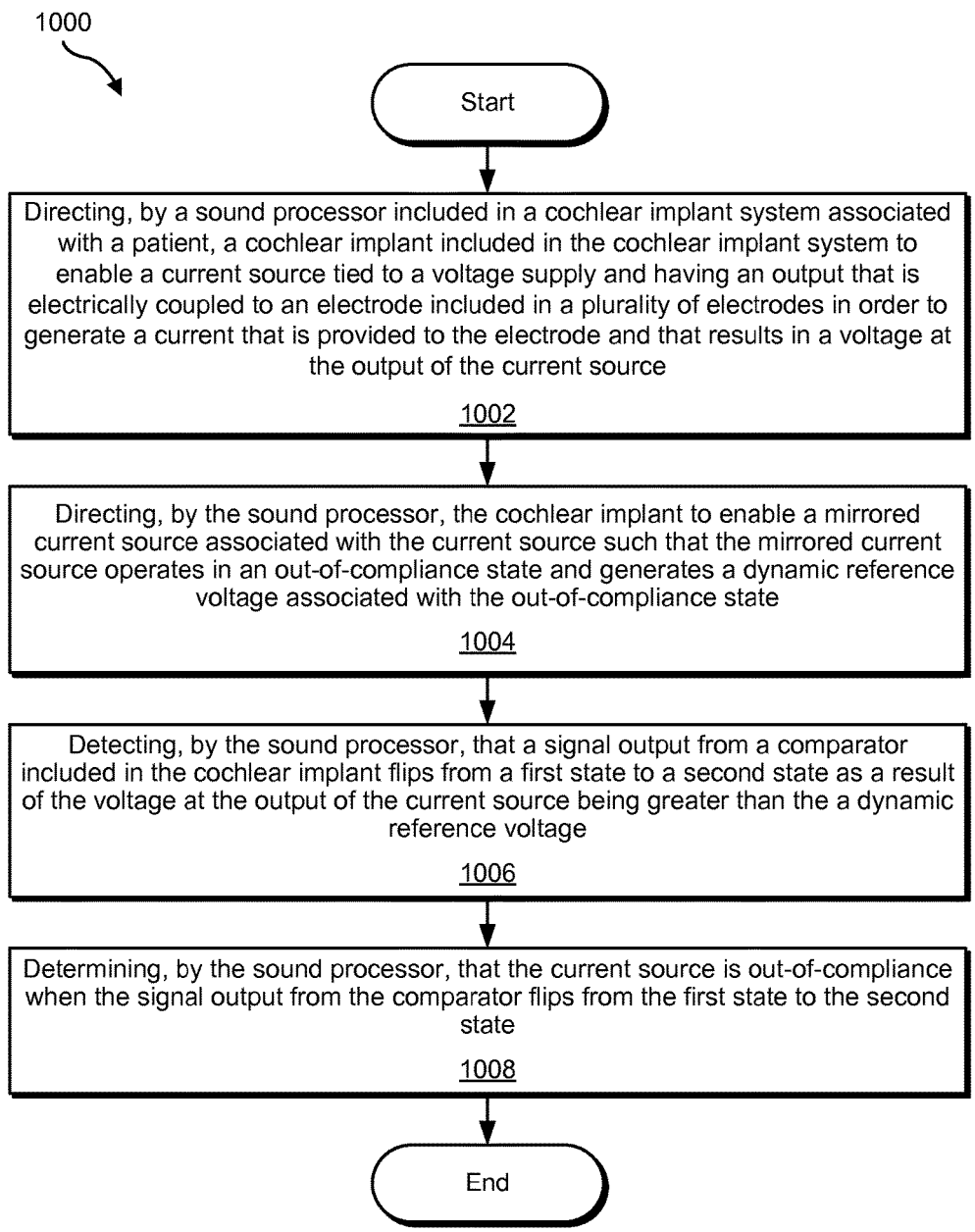
FIG. 10 illustrates an exemplary method for detecting a compliance state of a current source provided in a cochlear implant according to principles described herein.

FIG. 10 illustrates an exemplary method 1000 for detecting a compliance state of a current source. While FIG. 10 illustrates exemplary steps according to one embodiment, other embodiments may omit, add to, reorder, and/or modify any of the steps shown in FIG. 10. One or more of the steps shown in FIG. 10 may be performed by sound processor 104 and/or any implementation thereof.

In step 1002, a sound processor, included in a cochlear implant system associated with a patient, directs a cochlear implant included in the cochlear implant system to enable a current source tied to a voltage supply and having an output that is electrically coupled to an electrode included in a plurality of electrodes in order to generate a current that is provided to the electrode and that results in a voltage at the output of the current source. Step 1002 may be performed in any of the ways described herein.

In step 1004, the sound processor directs the cochlear implant to enable a mirrored current source associated with the current source such that the mirrored current source operates in an out-of-compliance state and generates a dynamic reference voltage associated with the out-of-compliance state. Step 1004 may be performed in any of the ways described herein.

In step 1006, the sound processor detects that a signal output from a comparator included in the cochlear implant flips from a first state to a second state as a result of the voltage at the output of the current source being greater than the a dynamic reference voltage. Step 1006 may be performed in any of the ways described herein.

In step 1008, the sound processor determines that the current source is out-of-compliance when the signal output from the comparator flips from the first state to the second state. Step 1008 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a cochlear implant that is electrically coupled to a plurality of electrodes, the cochlear implant being implanted within a patient and including
a current source tied to a voltage supply and having an output that is electrically coupled to an electrode included in the plurality of electrodes,
a mirrored current source associated with the current source and that is commanded to output a commanded current,
a reference load coupled to an output of the mirrored current source and that forces the mirrored current source into an out-of-compliance state in which the mirrored current source outputs a reference current that is a predetermined percentage lower than the commanded current, the reference current resulting in a dynamic reference voltage at the output of the mirrored current source, and
a comparator that
compares a voltage at the output of the current source with the dynamic reference voltage, and
outputs a signal based on the comparison, the signal indicative of a compliance state of the current source.

2. The system of claim 1, wherein the signal output by the comparator is output in one of a first state and a second state, the first state indicative of when the current source is in-compliance, and the second state indicative of when the current source is out-of-compliance.

3. The system of claim 2, wherein the current source is a positive current source, and wherein:
the comparator outputs the signal in the first state when the voltage at the output of the current source is less than the dynamic reference voltage; and
the comparator outputs the signal in the second state when the voltage at the output of the current source is greater than the dynamic reference voltage.

4. The system of claim 2, wherein the current source is a negative current source, and wherein:
the comparator outputs the signal in the first state when the voltage at the output of the current source is greater than the dynamic reference voltage; and
the comparator outputs the signal in the second state when the voltage at the output of the current source is less than the dynamic reference voltage.

5. The system of claim 2, further comprising a sound processor that directs the cochlear implant to adjust an amount of voltage provided by the voltage supply based on whether the signal output by the comparator is in the first state or the second state.

6. The system of claim 5, wherein, if the signal output by the comparator is in the second state, the sound processor directs the cochlear implant to increase the amount of voltage provided by the voltage supply.

7. The system of claim 5, wherein, if the signal output by the comparator is in the first state, the sound processor directs the cochlear implant to decrease the amount of voltage provided by the voltage supply.

8. The system of claim 1, wherein the reference load comprises a reference current source opposite in polarity to the mirrored current source, wherein the reference current source is configured to output a first current that is the predetermined percentage lower than the commanded current and that is configured to force the mirrored current source into the out-of-compliance state.

9. The system of claim 8, wherein the reference load further comprises an additional reference current source arranged in parallel with respect to the reference current source and that is configured to output a second current that has an amplitude that is lower than the first current.

10. The system of claim 9, wherein the additional reference current source is associated with a switch that, when closed, is configured to selectively enable the additional reference current source.

11. The system of claim 10, wherein the additional reference current source is configured such that closing the switch results in decreasing the predetermined percentage by a pre-defined amount.

12. The system of claim 1, wherein the reference load includes at least one resistor having a resistance value that is sufficient to force the mirrored current source into the out-of-compliance state.

13. The system of claim 1, wherein:
the current source comprises a plurality of unit cells; and
the mirrored current source comprises only a single unit cell corresponding to the plurality of unit cells of the current source.

14. The system of claim 1, further comprising a sound processor that commands a current from the current source, the current commanded from the current source resulting in the voltage at the output of the current source.

15. A system comprising:
a sound processor;
a cochlear implant that is electrically coupled to a plurality of electrodes, the cochlear implant being implanted within a patient and including
a current source tied to a voltage supply and having an output that is electrically coupled to an electrode included in the plurality of electrodes,
reference circuitry that outputs a dynamic reference voltage indicative of an out-of-compliance state associated with the current source, and
a comparator that compares a voltage at the output of the current source with the dynamic reference voltage and outputs a signal in one of a first state and a second state based on the comparison;
wherein
the sound processor commands a current from the current source,
the comparator, based on the current commanded by the sound processor, flips the signal from being output in the first state to being output in the second state when the voltage at the output of the current source is greater than the dynamic reference voltage, and
the sound processor determines, based on the signal flipping from the first state to the second state, that the current source has entered the out-of-compliance state, and
wherein the reference circuitry includes
a mirrored current source associated with the current source and that is commanded by the sound processor to output a second commanded current, and
a reference load coupled to an output of the mirrored current source.

16. The system of claim 15, wherein the reference load forces the mirrored current source to be in the out-of-compliance state by causing the mirrored current source to output a reference current that is a predetermined percentage lower than the second commanded current, the reference current resulting in the dynamic reference voltage being provided at the output of the mirrored current source.

17. The system of claim 16, wherein the reference load includes a reference current source opposite in polarity to the mirrored current source, wherein the reference current source is configured to output a first current that is the predetermined percentage lower than the second commanded current and that is configured to force the mirrored current source into the out-of-compliance state.

18. The cochlear implant of claim 17, the reference load also includes an additional reference current source arranged in parallel with respect to the reference current source and that is configured to output a second current that has an amplitude that is lower than the first current.

19. The cochlear implant of claim 18, wherein the additional reference current source is associated with a switch that, when closed, is configured to selectively enable the additional reference current source.

20. A method comprising:
    directing, by a sound processor included in a cochlear implant system associated with a patient, a cochlear implant included in the cochlear implant system to enable a current source tied to a voltage supply and having an output that is electrically coupled to an electrode included in a plurality of electrodes in order to generate a current that is provided to the electrode and that results in a voltage at the output of the current source;
    directing, by the sound processor, the cochlear implant to enable a mirrored current source associated with the current source such that the mirrored current source operates in an out-of-compliance state and generates a dynamic reference voltage associated with the out-of-compliance state, the mirrored current source operating in the out-of-compliance state based on a reference load coupled to an output of the mirrored current source;
    detecting, by the sound processor, that a signal output from a comparator included in the cochlear implant flips from a first state to a second state as a result of the voltage at the output of the current source being greater than the dynamic reference voltage; and
    determining, by the sound processor, that the current source is out-of-compliance when the signal output from the comparator flips from the first state to the second state.

* * * * *